United States Patent

Wade et al.

[11] 4,154,841
[45] May 15, 1979

[54] ANTIINFLAMMATORY 1-ACYL-3(5)-ALKYL-5(3)-PHENYL-1,2,4-TRIAZOLES

[75] Inventors: Peter C. Wade, Pennington, N.J.; B. Richard Vogt, Yardley, Pa.; Thomas P. Kissick, Princeton, N.J.

[73] Assignee: E. R. Squibb & Sons, Inc., Princeton, N.J.

[21] Appl. No.: 878,209

[22] Filed: Feb. 16, 1978

Related U.S. Application Data

[63] Continuation-in-part of Ser. No. 825,744, Aug. 18, 1977, Pat. No. 4,076,823.

[51] Int. Cl.$^2$ .................... A61K 31/41; C07D 249/08
[52] U.S. Cl. ........................... 424/269; 260/308 R; 260/465 R; 260/465 G
[58] Field of Search .................. 260/308 R; 424/269

[56] References Cited

U.S. PATENT DOCUMENTS 4,006,159   2/1977   Newman ..................... 260/308 R

FOREIGN PATENT DOCUMENTS 67130   6/1969   German Democratic Rep. ..... 260/308 R

OTHER PUBLICATIONS

Ikizler et al., Chem. Abstracts, vol. 86, Abstract No. 5535/w (1977).
Becker et al., II, J. Prakt. Chem., vol. 311, pp. 477–489 (1969).

*Primary Examiner*—Alton D. Rollins
*Attorney, Agent, or Firm*—Lawrence S. Levinson; Merle J. Smith; Burton Rodney

[57] ABSTRACT

1-Acyl-3(5)-alkyl-5(3)-phenyl-1,2,4-triazoles are provided having the structure

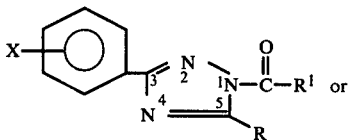 or

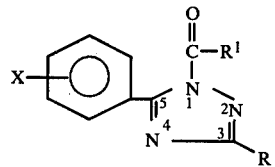

wherein R, R$^1$ and X are as defined hereinafter. These compounds are useful as antiinflammatory agents.

24 Claims, No Drawings

ANTIINFLAMMATORY 1-ACYL-3(5)-ALKYL-5(3)-PHENYL-1,2,4-TRIAZOLES

REFERENCE TO OTHER APPLICATION

This application is a continuation-in-part of application Ser. No. 825,744, filed Aug. 18, 1977, now U.S. Pat. No. 4,076,823.

BACKGROUND OF THE INVENTION

East German Pat. No. 67,130 to Becker et al describes a procedure for the synthesis of 3,5-disubstituted-1,2,4-triazoles useful as intermediates. The product triazoles are formed as follows. A starting material of structure I

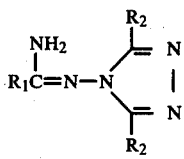

wherein $R_1$ is alkyl, aryl, aralkyl, alkoxyalkyl, acylaminoalkyl, or a heterocyclic group and $R_2$ is hydrogen, alkyl, or aryl, is treated with acylating agent such as an acid chloride or acid anhydride or an alkylating gent such as an alkylhalide. Depending on conditions, the product is isolated directly (or as its salt) or an intermediate product or residue of undefined structure or composition is first isolated and then converted to the triazole product by thermolysis or hydrolysis. A by-product is described in several examples which is a diacyl (or dialkyl) hydrazine presumably arising from the 1,2-hydrazino protion of the starting thiazole that is lost in the course of the reaction.

In Example 10 of the Becker et al patent, N-4-(3,5-dimethyl-1,2,4-triazolyl)benzamidine is reacted with acetic anhydride at 170° C. for 2-3 hours with evaporation of the volatile materials to form a residue ("Rückstand") of unknown composition and utility. The residue is heated for 3 hours in water to give the 3-methyl-5-phenyl-1,2,4-triazole product.

Becker et al neither identify the components of the residue nor separate out or isolate such components. However, it is believed that about one-half of the Rückstand or residue is a mixture of various by-products, and the remainder is a mixture of 1-acetyl-5-methyl-3-phenyl-1H-1,2,4-triazole and 1-acetyl-3-methyl-5-phenyl-1H-1,2,4-triazole in about a 90:10 ratio to each other.

Becker et al in a paper entitled "A Novel Synthesis for 3-Substituted 1,2,4-Triazoles," *Journal für praktische Chemie.* Volume 311, 1969, pages 477–489, disclose the preparation of 3-substituted-1,2,4-triazoles including 3-phenyl-1,2,4-triazoles of the structure

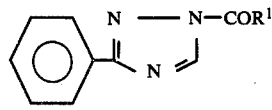

wherein $R^1$ can be ethoxy, methyl, ethyl or n-propyl. A general preparation for 1-acetyl-3-phenyl-1,2,4-triazole and 1-propionyl-3-phenyl-1,2,4-triazole is set out on page 487.

U.S. Pat. No. 4,006,159 to Newman discloses mixtures of acyl-substituted 1,2,4-triazole-3-carboxamides which may be presented by the following structural formulae:

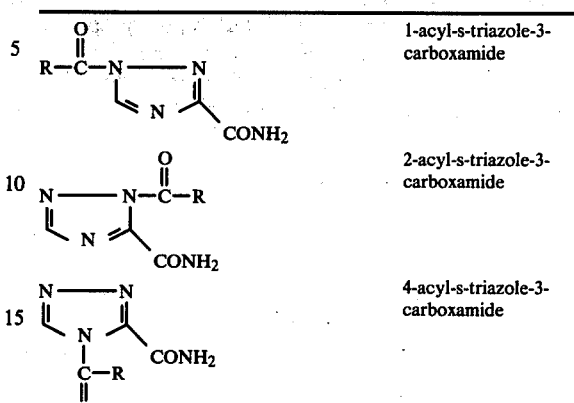

wherein each mixture consists of all three forms wherein R is the same in each form and wherein R is hydrogen, alkyl having up to 15 carbon atoms; cycloalkyl having from 3 to 8 carbon atoms; phenyl; ortho-, meta-, or para-hydroxyphenyl; ortho-, meta-, or paramethoxyphenyl; or adamantyl. The above mixture is said to be useful as anti-viral agents.

The present invention relates to 1-acyl-3(5)-alkyl-5(3)-phenyl-1,2,4-triazoles which are useful as antiinflammatory agents and have the structure

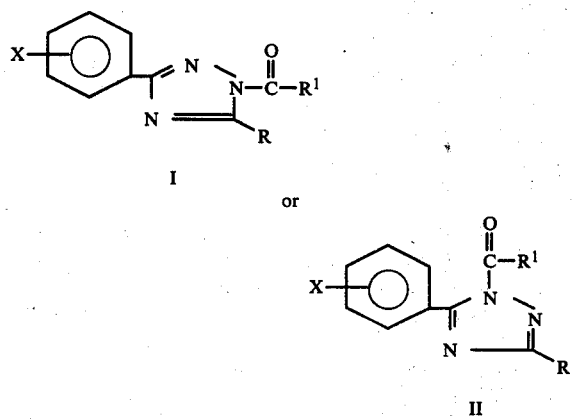

wherein R is lower alkyl or cycloalkyl, $R^1$ is lower alkyl or cycloalkyl, and X is hydrogen, halogen, lower alkyl, lower alkoxy, nitro or trifluoromethyl.

The preferred compounds of the invention are those of formula I wherein X is in the para position and is halogen, R is methyl or ethyl, and $R^1$ is methyl or ethyl.

The term "lower alkyl" as used herein refers to alkyl groups having 1 to 7 carbons, preferably 1 to 4 carbons, including straight or branched chain groups, such as methyl, ethyl, n-propyl, i-propyl, 2-propylbutyl, n-butyl, s-butyl, i-butyl, t-butyl, n-pentyl, n-hexyl, and n-heptyl and the various branched chain isomers thereof.

The term "lower alkoxy" as used herein refers to lower alkyl groups as defined above attached to an oxygen atom, with methoxy being preferred.

The term "cycloalkyl" as used herein refers to saturated carbocyclic radicals containing 3 to 7 carbons in the ring, such as cyclopropyl, cyclobutyl, cyclopentyl, cyclohexyl or cycloheptyl.

The term "halogen" as employed herein refers to chlorine, bromine, iodine or fluorine with chlorine and bromine being preferred.

The compounds of formulae I and II may be prepared according to a modification of the procedure outlined in East German Pat. No. 67,130 (1969), *Chem. Abst.* 71, 124441e. Thus, a benzonitrile of the structure

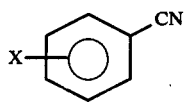   III is condensed with an amino-1,2,4-triazole of the structure

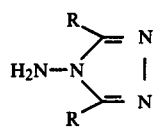   IV in the presence of an alkali metal hydride, such as sodium hydride or lithium hydride, and a non-reacting solvent such as dimethylformamide, dimethyl sulfoxide or dioxane, to form a compound of the structure

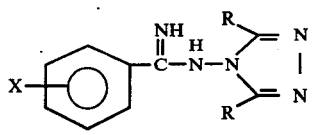   V

The formula V compound is then reacted with an acid anhydride

   VI such as acetic anhydride, propionic anhydride, butyric anhydride and the like to yield a mixture of the formulae I and II compounds of the invention.

The mixture may be separated into the formula I compund and the formula II compound by crystallization from an appropriate solvent, such as ethanol or isopropyl ether or by chromatography on a suitable adsorbent, such as silica gel. The formulae I and II compounds may be separately recovered in crystalline form each at least 95% and preferably 99% pure.

The starting triazole of structure IV is prepared by techniques well known in the art (e.g., see Th. Curtius and G. M. Dedichen, *J. Prakt. Chem.,* 50, 241 (1894), Beil. 26, 29). Thus, the formula IV compound may be prepared by reaction of hydrazine and an alkyl cyanide VII RCN wherein R is lower alkyl or cycloalkyl, under high temperatures ranging from 100 to 250, preferably from 140° to 190° C., for periods of 0.5 to 48 hours in a sealed system, if necessary.

The compounds of formula I have antiinflammatory activity as measured by the mouse active arthus (MAA) test and/or other related tests and are useful as antiinflammatory agents and may be used, for example, in a manner similar to phenylbutazone or indamethacin. They may be used to decrease joint swelling, tenderness, pain and stiffness in mammalian species, e.g., in conditions such as rheumatoid arthritis. The quantity administered ranges from about 1 mg to about 150 mg per kg and preferably from about 5 mg to about 75 mg per kg of body weight per day.

A compound of formula I or II can be administered orally or parenterally (for example, intraperitoneally, subcutaneously, intramuscularly or intravenously). Powders can be prepared by comminuting the active ingredient with a similarly comminuted diluent such as starch or lactose. Suitable forms for oral administration include capsules, tablets, troches, elixirs, wafer, chewing gum, syrups, and a suitable form for parenteral administration in a sterile injectable. Such unit dosage forms are prepared by compounding with a conventional vehicle, excipients, binders, preservatives, stabilizers, flavoring agents or the like as called for by acceptable pharmaceutical practice. Also, the compounds used in this invention can be formulated with other pharmaceutically active compounds.

The tablets, troches, pills, capsules and the like may also contain the following: a binder such as gum tragacanth, acacia, corn starch or gelatin; an excipient such as dicalcium phosphate, a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain in addition to materials of the above type a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

The following examples are illustrative of the invention and represent preferred embodiments. Other modifications may be readily produced by suitable variations of the reactions. All temperatures are on the Centigrade scale.

EXAMPLE 1

1-Acetyl-3-(4-chlorophenyl)-5-methyl-1H-1,2,4-triazole

A. 4-Amino-3,5-dimethyl-4H-1,2,4-triazole

Hydrazine hydrate (N₂H₄·H₂O, 100 g, 2.0 mol) and acetonitrile (75 g, 1.8 mol) are weighed out into a bomb which is sealed and heated at 150° for eight hours. The reaction mixture is heated at 180° (pressure rises to 420 lb/in²) overnight. After the bomb is cooled, vented and opened, a white solid plus some liquid remains. The solid is collected on a filter washed with a small amount of cold water, toluene, and recrystallized from 600 ml of ethyl acetate to give 51 g of the title A compound, m.p. 195°-197° C.

B.

4-Chloro-N-(3,5-dimethyl-4H-1,2,4-triazol-4-yl)-benzenecarboximidamide 15.32 g (364 mM) Sodium hydride (57% oil dispersion) is washed with ether (X 5) in a sintered glass funnel to remove the oil. The free sodium hydride is washed with a little DMSO into a stirred suspension of 50.0 g (363 mM) of 4-chlorobenzonitrile and 40.7 g (363 mM) of 4-amino-3,5-dimethyl-4H-1,2,4-triazole (prepared in part A) in 200 ml of DMSO (distilled from CaH$_2$ under vacuum). After the addition, the mixture is stirred in an ice bath for 1 hour and for 3 hours at room temperature. The reaction mixture is poured into 2 liters of ice water and stirred for 15 minutes until the floculant precipitate coagulates into a filterable state. The product is then filtered out, washed with water, and dried at 50° under vacuum overnight to yield 94.2 g of the title B compound, m.p. 303°–306°. (This material is suitable for use in part C.)

C.
1-Acetyl-3-(4-chlorophenyl)-5-methyl-1H-1,2,4-triazole 63.6 g (254.0 mM) 4-Chloro-N-(3,5-dimethyl-4H-1,2,4-triazol-4-yl)benzenecarboximidamide prepared in part B and 67 ml of acetic anhydride in a 300 ml round bottom flask equipped with a distillation head are heated to 170° in an oil bath. A solution forms from which acetic acid distills off in the first few minutes. The mixture is refluxed for 2.5 hours and the excess acetic anhydride is evaporated to dryness under vacuum to produce a residue comprising a mixture of the title compound and its 1-acetyl-5-(4-chlorophenyl)-3-methyl isomer. The residue is triturated with 120 ml of water at room temperature and filtered. The filter cake is dissolved in 1 liter of hot ethanol, filtered hot, and the product precipitated from the hot alcohol by adding 3 liters of cold water. The product is filtered off, wshed with water, and dried at 80° under vacuum to yield 37.6 g of the 1-acetyl-3-(4-chlorophenyl)-5-methyl-1H-1,2,4-triazole as a crystalline material (99% pure), m.p. 132°–133°.

The filtrate is evaporated under vacuum to dryness to yield a mixture of 1-acetyl-5-(4-chlorophenyl-3-methyl and 1-acetyl-3-(4-chlorophenyl)-3-methyl isomers and the corresponding deacetylated triazole. The mixture is chromatographed on silica gel preparative TLC plates using a chloroform:ethyl acetate mixture (3:2) to yield additional 1-acetyl-3-(4-chlorophenyl)-5-methyl isomer as the high R$_f$ and the 1-acetyl-5-(4-chlorophenyl)-3-methyl isomer as the next band (slightly lower R$_f$).

EXAMPLE 2

3-(4-Chlorophenyl)-5-methyl-1-(oxopropyl)-1H-1,2,4-triazole 5.0 g (0.022 mol) 4-Chloro-N-(3,5-dimethyl-4H-1,2,4-triazol-4-yl)-benzene carboximidamide prepared as described in Example 1B and 10 ml propionic anhydride are combined and heated in an oil bath at 170°–190° C. The mixture forms a solution and after 2 hours, a vacuum is cautiously applied to remove the volatiles. The residue is taken up in CHCl$_3$ and chromatographed on a silica gel column (5×20cm) with CHCl$_3$. The first band eluted is collected (followed by TLC) and the solvents evaporated to yield 3.9 g (71%) of residue which comprises a mixture of the title compound and its 5-(4-chlorophenyl)-3-methyl-1-(oxopropyl)-1,2,4-triazole isomer. This material is recrystallized from 100 ml of absolute ethanol with cooling to 25° to yield 2.6 g of the title compound which after drying at 40° (1 torr) yields crystals (99% pure) melting at 108°–109°.

Evaporation of the filtrate and rechromatography on preparative TLC plates using a chloroform:ethyl acetate (3:2) yields the title compound as the high R$_f$ and its 5-(4-chlorophenyl)-3-methyl-1-(oxopropyl) isomer as the next band (slightly lower R$_f$).

EXAMPLES 3 to 16

Following the procedure of Example 1 but substituting for 4-chloro benzonitrile, the compound shown in Column I of Table A below, substituting for the aminotriazle, the compound shown in Column II, and substituting for the acetic anhydride, the compound shown in Column III, the compound of the invention shown in Column IV is obtained.

The corresponding isomer is obtained in accordance with the procedure outlined in Example 1, part C.

It will be appreciated that in Examples 3 to 16 the corresponding 5-phenyl-3-R-1-acyl isomers are also separately obtained.

TABLE A

| Ex. No. | Column I | | Column II | | Column III R$^1$—C(O)—O—C(O)—R$^1$ | Column IV | | |
|---|---|---|---|---|---|---|---|---|
| | X (position) | | R | | | X (position) | R | R$^1$ |
| 3. | H | | CH$_3$ | | CH$_3$ | As in Column I | As in Column II | As in Column III |
| 4. | Br(2) | | C$_2$H$_5$ | | C$_2$H$_5$ | | | |
| 5. | CH$_3$(3) | | CH$_3$ | | △S | | | |
| 6. | CH$_3$O(4) | | C$_2$H$_5$ | | (CH$_3$)$_2$CH(CH$_2$)$_4$— | | | |
| 7. | CF$_3$(4) | | CH$_3$ | | C$_2$H$_5$ | | | |
| 8. | NO$_2$(3) | | n-C$_3$H$_7$ | | CH$_3$ | | | |
| 9. | H | | △S | | n-C$_4$H$_9$ | | | |
| 10. | Cl(2) | | C$_2$H$_5$ | | C$_2$H$_5$ | | | |
| 11. | C$_2$H$_5$(3) | | C$_2$H$_5$ | | t-C$_4$H$_9$ | | | |
| 12. | C$_2$H$_5$O(4) | | n-C$_4$H$_9$ | | n-C$_5$H$_{11}$ | | | |
| 13. | NO$_2$(2) | | CH$_3$ | | CH$_3$ | | | |

TABLE A-continued

| | Column I | Column II | Column III | Column IV | | |
|---|---|---|---|---|---|---|
| Ex. No. | X (position) | R | $R^1-\overset{O}{\underset{\|}{C}}-O-\overset{O}{\underset{\|}{C}}-R^1$ | X (position) | R | $R^1$ |
| 14. | CF$_3$(2) | C$_2$H$_5$ |  | As in Column I | As in Column II | As in Column III |
| 15. | H |  | CH(CH$_2$CH$_2$CH$_3$)$_2$ | | | |
| 16. | H |  | n-C$_3$H$_7$ | | | |

EXAMPLE 17

Parenteral Composition Containing 1-Acetyl-3-(4-Chlorophenyl)-5-methyl-1H-1,2,4-triazole A dispersion suitable for parenteral administration is prepared by dispersing 1 mg of 1-acetyl-3-(4-chlorophenyl)-5-methyl-1H-1,2,4-triazole in about 100 ml of water for injection.

EXAMPLE 18

Tablets Containing 1-Acetyl-3-(4-chlorophenyl)-5-methyl-1H-1,2,4-triazole

The following ingredients are used to make 1,000 200 mg tablets each containing 100 mg of active ingredient:

| | | |
|---|---|---|
| 1-Acetyl-3-(4-chlorophenyl)-5-methyl-1H-1,2,4-triazole | 100 | gm |
| Polyvinyl pyrrolidone | 7.5 | gm |
| Lactose | 20 | gm |
| Magnesium stearate | 3.5 | gm |
| Corn starch | 17.5 | gm |
| Avicel (microcrystalline cellulose) | 51.5 | gm |

The medicament and lactose are thoroughly admixed, the polyvinyl pyrrolidone is dissolved in ethanol USP to make a 30% solution. This solution is used to granulate the mixture of medicament and lactose. The granulation is passed through a No. 16 screen and air dried. The dried granulation is then passed through a No. 20 screen. To the screened granulate are added the magnesium stearate, Avicel and the corn starch and the mixture is blended. The blend is then compressed into 200 mg tablets on a standard concave punch. The tablets are then veneer coated with methyl cellulose in a spray gun.

What is claimed is:

1. A compound of the structure

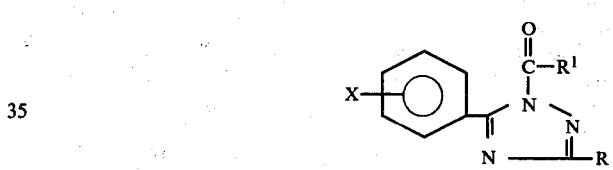

wherein R is lower alkyl or cycloalkyl containing 3 to 7 carbons; $R^1$ is lower alkyl, or cycloalkyl containing 3 to 7 carbons, and X is lower alkoxy, halogen, or trifluoromethyl.

2. The compound of claim 1 wherein X is in the 3- or 4-position.

3. The compound of claim 1 wherein X is halogen.

4. The compound of claim 2 wherein X is halogen and is in the 4-position.

5. The compound of claim 4 wherein R is lower alkyl, $R^1$ is methyl or ethyl.

6. The compound of claim 1 wherein X is lower alkoxy, or trifluoromethyl.

7. The compund of claim 1 having the formula

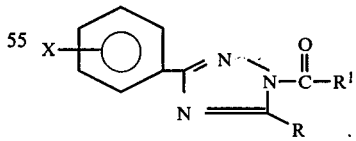

8. The compound of claim 1 having the formula

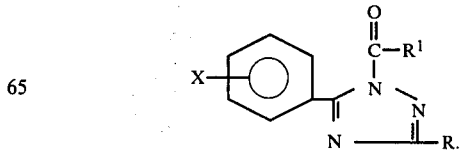

9. The compound as defined in claim 1 in crystalline form at least 95% pure.

10. The compound of claim 1 having the name 1-acetyl-3-(4-chlorophenyl)-5-methyl-1H-1,2,4-triazole.

11. The compound as defined in claim 10 in crystalline form at least 95% pure.

12. The compound as defined in claim 10 having a melting point of 132°–133° C.

13. The compound of claim 1 having the name 3-(4-chlorophenyl)-5-methyl-1-(oxopropyl)-1H-1,2,4-triazole.

14. The compound as defined in claim 13 in crystalline form at least 95% pure.

15. The compound as defined in claim 13 having a melting point of 108°–109° C.

16. An anti-inflammatory composition which comprises an anti-inflammatory amount of a compound of the structure

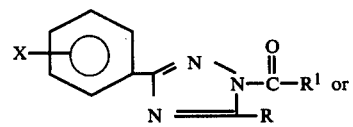 or

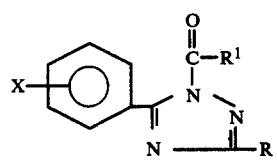

wherein R is lower alkyl or cycloalkyl, R¹ is lower alkyl, or cycloalkyl, and X is hydrogen, lower alkyl, lower alkoxy, hlogen, nitro or trifluoromethyl, in a physiologically acceptable vehicle.

17. The composition as defined in claim 16 wherein the compound has the structure

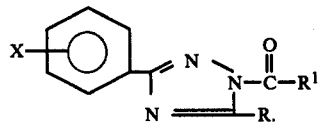

18. The composition as defined in claim 16 wherein the compound has the name 1-acetyl-3-(4-chlorophenyl)-5-methyl-1H-1,2,4-triazole or 3-(4-chlorophenyl)-5-methyl-1-(oxopropyl)-1H-1,2,4-triazole.

19. The composition as defined in claim 16 wherein said compound comprises a mixture of compounds of the structures

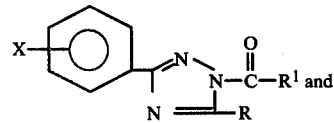

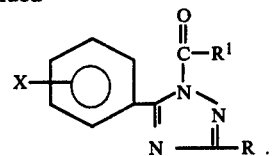

20. A method for treating an inflammatory condition in a mammalian host, which comprises administering an effective amount of a compound of the structure

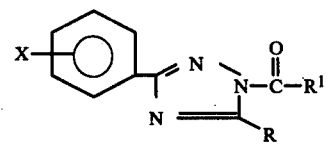

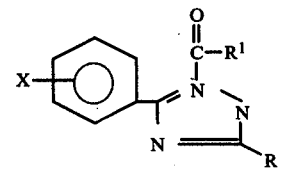

wherein R is lower alkyl or cycloalkyl having 3 to 7 carbons, R¹ is lower alkyl, or cycloalkyl having 3 to 7 carbons, and X is hydrogen, lower alkyl, lower alkoxy, halogen, nitro or trifluoromethyl.

21. The method as defined in claim 20 wherein the compound has the structure

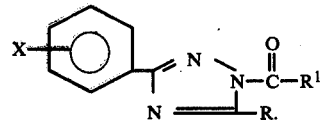

22. The method as defined in claim 20 wherein the compound is employed in conjunction with a physiologically acceptable carrier.

23. The method as defined in claim 20 wherein said compound has the name 1-acetyl-3-(4-chlorophenyl)-5-methyl-1H-1,2,4-triazole or 3-(4-chlorophenyl)-5-methyl-1-(oxopropyl)-1H-1,2,4-triazole.

24. The method as defined in claim 20 wherein said compound comprises a mixture of compounds of the structure

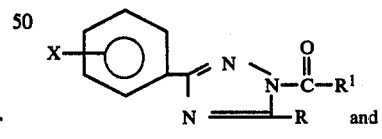 and

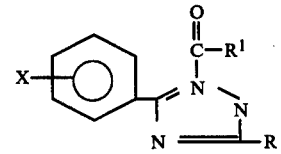

* * * * *

UNITED STATES PATENT OFFICE
CERTIFICATE OF CORRECTION

Patent No. 4,154,841                        Dated May 15, 1979

Inventor(s) Peter C. Wade et al.

It is certified that error appears in the above-identified patent and that said Letters Patent are hereby corrected as shown below:

Column 1, line 28, "gent" should read --agent--.
Column 1, line 36, "protion" should read --portion--.
Column 3, line 64, "indamethacin" should read --indomethacin--.
Column 5, line 28, "wshed" should read --washed--.
Column 6, line 33, "triazle" should read --triazole--.
Column 10, the second structure in Claim 20 should read as follows:

-- 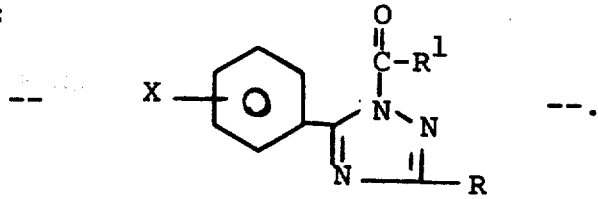 --.

Column 10, the second structure in Claim 24 should read as follows:

-- 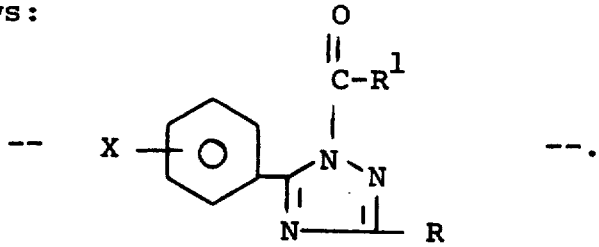 --.

Signed and Sealed this

Sixth Day of November 1979

[SEAL]

Attest:

RUTH C. MASON
Attesting Officer

LUTRELLE F. PARKER
Acting Commissioner of Patents and Trademarks